United States Patent [19]
Keith

[11] Patent Number: 5,087,394
[45] Date of Patent: Feb. 11, 1992

[54] METHOD FOR FORMING AN INFLATABLE BALLOON FOR USE IN A CATHETER

[75] Inventor: Peter T. Keith, Edina, Minn.

[73] Assignee: SciMed Life Systems, Inc., Maple Grove, Minn.

[21] Appl. No.: 434,031

[22] Filed: Nov. 9, 1989

[51] Int. Cl.⁵ .................... B29C 49/14; B29C 55/22
[52] U.S. Cl. ........................ 204/22; 264/291; 264/521; 264/532; 264/DIG. 33; 264/DIG. 66; 264/DIG. 73; 425/529; 425/393; 425/DIG. 53
[58] Field of Search .......... 264/532, 521, 209.5, 264/291, DIG. 33, DIG. 73, DIG. 66, 210.7, 292, 22; 425/529, 392, 393, DIG. 53

[56] References Cited

U.S. PATENT DOCUMENTS

| | | | |
|---|---|---|---|
| 2,690,595 | 10/1954 | Raiche | 18/58.7 |
| 3,304,353 | 2/1967 | Harautuneian | 264/98 |
| 3,985,601 | 10/1976 | Panagrossi | 604/103 |
| 4,093,484 | 6/1978 | Harrison et al. | 156/244.13 |
| 4,130,617 | 12/1978 | Wallace | 425/529 |
| 4,154,244 | 5/1979 | Becker et al. | 128/349 B |
| 4,195,637 | 4/1980 | Grüntzig et al. | 128/348 |
| 4,254,774 | 3/1981 | Boretos | 128/348 |
| 4,380,525 | 4/1983 | Jakobsen et al. | 264/521 |
| 4,490,421 | 12/1984 | Levy | 128/344 |
| 4,497,074 | 2/1985 | Rey et al. | 3/1 |
| 4,547,416 | 10/1985 | Reed et al. | 264/532 |
| 4,580,968 | 4/1986 | Jakobsen et al. | 264/532 |
| 4,735,538 | 4/1988 | Reed et al. | 264/532 |
| 4,737,219 | 4/1988 | Taller et al. | 156/215 |
| 4,801,419 | 1/1989 | Ward et al. | 425/393 |

FOREIGN PATENT DOCUMENTS

| | | | |
|---|---|---|---|
| 1324241 | 3/1963 | France . | |
| 63-007927 | 1/1988 | Japan | 264/532 |
| 773971 | 5/1957 | United Kingdom . | |
| 2003081 | 3/1979 | United Kingdom | 264/532 |

OTHER PUBLICATIONS

Adrova et al., *Polyimides—A New Class of Heat-Resistant Polymers*, Israel Program for Scientific Translations, Jerusalem 1969, pp. 4–13.

Primary Examiner—Jan H. Silbaugh
Assistant Examiner—Catherine Timm
Attorney, Agent, or Firm—Kinney & Lange

[57] ABSTRACT

A method for forming an inflatable catheter balloon from an initial length of tubing includes longitudinally stretching a first end segment of the tubing element and longitudinally stretching a second end segment of the tubing element. The longitudinally stretched tubing is then heated, blow-molded to radially stretch it and define a desired inflatable portion for the balloon, and cooled.

11 Claims, 3 Drawing Sheets

METHOD FOR FORMING AN INFLATABLE BALLOON FOR USE IN A CATHETER

BACKGROUND OF THE INVENTION

The present invention relates to the field of angioplasty and in particular, to new and improved catheters for performing balloon angioplasty procedures on blood vessels.

Angioplasty has gained wide acceptance in recent years as an efficient and effective method for treating vascular diseases. In particular, angioplasty is widely used for opening a stenosis in the coronary arteries, and is also used for treatment of a stenosis in other parts of the vascular system.

The most widely used method of angioplasty makes use of a dilatation catheter which has an inflatable balloon at a distal end. Using an x-ray fluoroscope, a physician guides the catheter through the vascular system until the balloon is positioned across the stenosis. The balloon is subsequently inflated, exerting pressure radially and outwardly against the stenosis, causing the artery wall to stretch and re-establishing an acceptable blood flow through the artery.

In order to treat a stenosis having a very small opening, there has been continuing efforts to reduce the profile of dilatation catheters so that the catheter not only can reach but also can cross such a very tight stenosis. An important factor in determining the profile of a dilatation catheter is the wall thickness of the balloon material. Another important factor concerning profile is the diameter and flexibility of the proximal and distal ends of the balloon. A balloon having a reduced diameter and a more flexible distal end permits an easier "start" into the stenosis and thus provides a greater likelihood that the balloon can be properly positioned across the stenosis.

A typical method of manufacturing a balloon for use in a dilatation catheter generally begins by extruding a tubing material from an extruder using a particular draw-down ratio and rate of extrusion. The size of the extruder, draw-down ratio, and rate of extrusion determine the inner and outer dimensions of the tubing material. The dimensions are adjusted according to a desired balloon size (e.g., 2.0, 2.5, 3.0, 3.5 mm) and desired balloon burst strength (e.g., 12 or 14 atm).

The extruded tubing, upon cooling, is irradiated (e.g., exposed to electron beam radiation) which changes the mechanical properties of the tubing to increase its strength and control compliance characteristics of the balloon. The tubing is cut into segments and placed into a blow-mold cavity wherein an intermediate segment of the tubing is heated and pressurized to expand radially outwardly, thereby becoming a distensible main body portion of the balloon. The distal and proximal "waists" of the tubing/balloon are also heated and blown out in the mold, as needed, in order to get the inner diameters of the waists to suitable dimensions for bonding those ends onto the other catheter components. Thus, the balloon has narrow distal and proximal segments relative to an enlarged main body portion.

Once the balloon is formed, a proximal end thereof is attached to a distal end of a catheter tube. Typically, a proper bond is achieved by overlapping a distal end segment of the catheter tube with a larger diameter proximal end segment of the proximal waist of the balloon, and providing a suitable adhesive bond therebetween.

Current balloon manufacturing methods require that each balloon size and strength combination utilize a tubing material with specific inner and outer dimensions. This requirement allows proper formation of the distensible portion of the balloon. One drawback to this situation is that the proximal and distal segments of the tubing element forming the balloon are restricted to the dimensions of the original tubing material. Also, during the heating and pressurizing process used to form the distensible portion of the balloon, the internal heat and pressure consequently increase the dimensions of the proximal and distal segments of the tubing element in order to get the desired inner diameter. Thus, the proximal and distal segments typically end up having diameters which are larger than desired, and potentially larger than what the folded balloon profile can be when fully folded down. This problem becomes more pronounced as catheter tube diameters are reduced in an effort to minimize catheter profiles and when larger distensible balloon portions are needed (because the dimensions of original tubing must increase as the distensible portion of the balloon is increased). In other words, the problems of large diameter waist segments becomes more pronounced as the other catheter elements become smaller.

Another disadvantage from balloons formed by current methods stems from the thickness of the proximal and distal ends. When the intermediate segment is heated and pressurized, the balloon walls forming the distensible portion of the balloon become thinner. This thinning is taken into account when determining the variables (rate of the extrusion, extruder size, and draw-down ratio) of the extrusion process. Thus, the balloon material is extruded at a thickness which is greater than the finished balloon. Because the proximal and distal ends will expand only slightly during balloon formation (with a slight decrease in wall thickness), the thicker material in the proximal and distal ends reduce the flexibility of the balloon and contributes to a larger balloon profile.

In an effort to reduce balloon profile and to protect the balloon, a protective sleeve, preferably formed of plastic having an inner surface coated with a lubricious coating, is placed over the balloon. The sleeve is threaded onto the balloon from its distal end, causing the walls of the balloon to fold and wrap tightly around the guide wire (in a fixed-wire catheter) or an inner core which contains the guide wire (in an over-the-wire catheter). The sleeve is removed just prior to inserting the catheter into a patient. The compression caused by the sleeve reduces the balloon's profile allowing the catheter to cross tighter and tighter lesions. It is desirable to have the distal balloon waist considerably smaller than the diameter of a fully "compressed" or "wrapped" balloon. Having the waist smaller means that the "crossing profile" of the balloon is determined by the diameter of the folded balloon diameter, rather than the diameter of the distal waist outer diameter. A thicker and less flexible distal waist thus prohibits smaller diameter sleeves from being placed onto the balloon, and causes an unnecessary increase in balloon profile because the balloon cannot be fully compressed.

Another disadvantage concerns crossing the stenosis once the sleeve is removed. Thinner and more flexible proximal and distal waists on the balloon allow an easier "start" into the stenosis, providing a better chance that the balloon can be effectively advanced across the lesion. On the other hand, a thicker distal waist causes the balloon to bunch as it enters the stenosis, further reducing the ability of the balloon to be properly positioned.

The disadvantages described above have presented substantial difficulties for dilatation balloon catheter manufacturers working to reduce the profiles of catheter balloons. The disadvantages are especially prevalent in fixed-wire catheters which are typically designed for tight stenosis procedures. Thus, there is a need to manufacture a balloon having a distensible portion with the proper size and strength characteristics for dilation procedures while providing flexible small diameter proximal and distal ends to minimize the disadvantages described above. Heretofore, however, manufacturing techniques to accomplish this goal had not been developed.

SUMMARY OF THE INVENTION

Unlike previous balloon manufacturing methods which lack the ability to reduce the diameters of the proximal and distal ends of the balloon while satisfying the requirements of the distensible portion of the balloon, the present invention is a method whereby these diameters are reduced, the flexibility of the balloon is enhanced, and the size and strength characteristics of the distensible portion of the balloon are maintained.

The present invention is a method for forming a tubing element for use in a balloon dilatation catheter wherein the tubing element has a first end segment, an intermediate segment and a second end segment. The inventive method includes stretching the first end segment of the tubing element. In a preferred embodiment, the second end segment of the tubing element is also then stretched.

Preferably, the stretching of the first end segment of the tubing element includes positioning an internal support mandrel having a first diameter within the second end segment and the intermediate segment of the tubing element. A body clamp is attached about the support mandrel and the intermediate segment of the tubing adjacent a distal end of the support mandrel. An end clamp is then attached adjacent an outer end of the first end segment. The first end segment is heated the body clamp and end clamp are urged apart to stretch the first end segment. The heating and urging steps may be repeated one or more times depending upon the desired inner and outer dimensions of the tubing element. The first end segment is then cooled.

To stretch the second end segment, an internal support mandrel having a second diameter is positioned within the first end and intermediate segments of the tubing element. The second-diameter mandrel has a smaller diameter than the first-diameter mandrel so that the second-diameter mandrel can be positioned within the already stretched first end segment of the tubing element. The body clamp is attached about the support mandrel and intermediate segment of the tubing adjacent a distal end of the support mandrel. The end clamp is attached adjacent an outer end of the second end segment. Heat is applied to the second end segment while urging the body and end clamps apart. The heating and urging steps may be repeated one or more times depending upon the desired inner and outer dimensions of the tubing element. The second end segment is then cooled.

Once the tubing element has been stretched, it is aligned in an enlarged diameter cavity, with each end thereof fixed relative to the cavity. The tubing element is heated and pressurized so that it expands outwardly into the cavity to create the distensible portion of the balloon and also to attain the desired inner diameters for the end segments thereof. Finally, the tubing element is cooled.

DETAILED DESCRIPTION OF THE PREFERRED EMBODIMENTS

Figure 1:
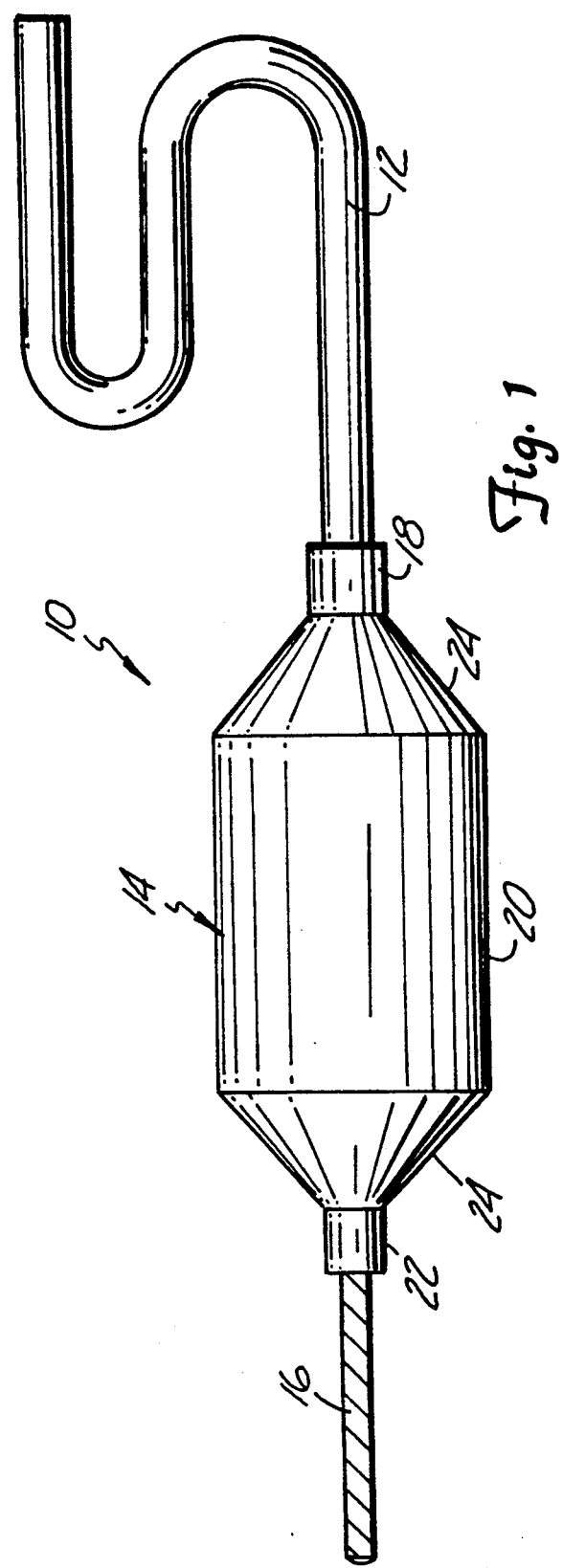
FIG. 1 is illustrates a balloon dilatation catheter utilizing a balloon formed by the method of the present invention.

Catheter 10, as shown in FIG. is a balloon dilatation catheter which includes a flexible shaft 12, a balloon 14 and a flexible distal tip 16. In FIG. 1, balloon 14 is shown in its fully inflated condition. Depending upon the particular construction of the catheter 10 (i.e., whether it is over-the-wire or fixed-wire), tip 16 may be the distal end of a movable guide wire which extends through the shaft 12 and the balloon 14, or tip 16 may be the distal end of a fixed-wire or core which is bonded to the balloon 14 or shaft 12.

Shaft 12, which is preferably a metal or polymeric tube, has at least one lumen extending from its proximal to its distal end. Depending upon the construction of catheter 10, multiple lumens may be provided in shaft 12. In any case, however, at least an inflation lumen extends through the shaft 12 for selective inflation and deflation of the balloon 14.

Balloon 14, which is preferably formed of a polymer material such as polyolefin, has a proximal or a waist segment 18, a distensible balloon segment 20 and a distal segment 22 (which typically has a smaller outer diameter than waist segment 18). Waist segment 18 is bonded to a distal end of shaft 12, preferably by an adhesive seal such as epoxy. The distal segment 22 is bonded to an inner tube (not shown) containing a guide wire in an over-the-wire catheter or to the tip 16 in a fixed-wire catheter. The distensible portion of segment 20 has cone-shaped end portions 24 which taper to meet waist segment 18 and distal segment 22, and is expandable upon inflation of the balloon 14 to assume a desired profile for dilatation.

The formation of a balloon 14 is a multi-step process. Initially, a length of polymer tubing is formed by drawing a tubing material from an extruder using a predetermined draw-down ratio and rate of extrusion. The size of the extruder die, draw-down ratio and rate of extrusion determine the characteristics of the distensible portion 20 of the balloon 14. Thus, each can be adjusted to form a tubing material that once formed into a balloon, will yield a desired balloon size and strength.

Because further stretching of the tubing material will occur, a low draw-down ratio or speed of extrusion is desired. Lowering these parameters results in a lowering of the axial molecular orientation of the polymer material of the tubing and, therefore, the tubing material will have a higher percent elongation (it will be more stretchable before breakage). A preferred draw-down ratio is 2:1.

Once extruded, the tubing material is cut into a plurality of tubing elements 26. A balloon is then formed by the inventive method from each of the tubing elements 26. Each tubing element 26 (initially a length of uniform inside and outside diameter tubing) has a first end segment 28 (shown generally in FIGS. 2 and 3) and a second end segment 30 (shown generally in FIGS. 4 and 5), both of which will be stretched. An intermediate segment 20 is provided between the end segments 28 and 30, and will be formed into the inflatable portion of the balloon 14.

Figure 2:
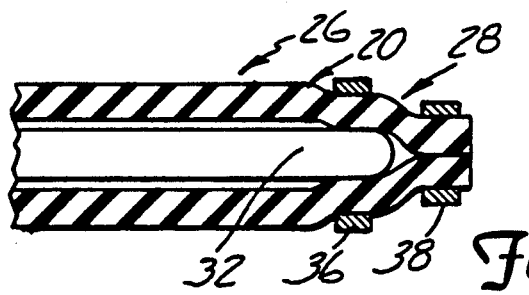
FIG. 2 illustrates a partial side view, in section, of a first end portion of a tubing element which will be used to fabricate a balloon in accordance with the present invention, prior to stretching thereof.

A preferred method for stretching the tubing segment 26, as shown in FIGS. 2-5, is initiated by positioning an internal support mandrel 32 having a first diameter within the first end segment 28 and the intermediate segment 20 of tubing element 26 (as shown in FIG. 2). A body clamp 36 is mounted about a distal end of the support mandrel 32, compressing a portion of the intermediate segment 20 onto the support mandrel 32, which is provided to prevent pinching or flattening of the tubing element 26 by the body claim 36. An end clamp 38 is then mounted about an outer end of the first end segment 28, and the first end segment 28 is heated while urging the body clamp 36 and end clamp 38 longitudinally apart (as shown by arrow 29 in FIG. 3). The separation of the clamps pulls on and stretches the heated first end segment 28, then assumes a smaller inner and outer diameter. As the cross-sectional dimensions of the first end segment 28 are reduced, the clamps also constrict to maintain their grip on the first end segment 28.

Figure 3:
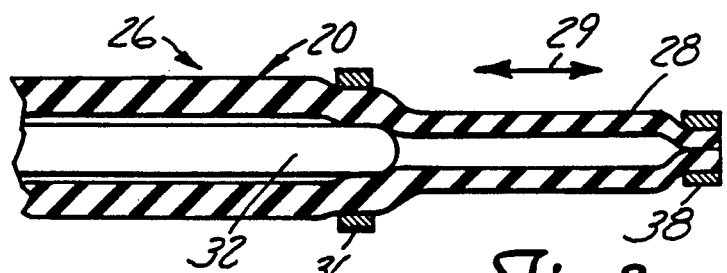
FIG. 3 illustrates the tubing element in FIG. 2 after the first end portion thereof has been stretched.

As illustrated in FIG. 3, the tubing element 26 thus stretches down to a smaller size between the clamps 36 and 38, which are made or coated with rubber or some other pliable material so the tubing element 26 is not damaged by the clamps. Variations in the amount of stretch can be achieved with alternative selections of heating times and temperatures or by repeating the number of heating and urging cycles, but is primarily determined by selecting the amount of longitudinal elongation between the clamps. Once the first end segment 28 has been worked by stretching and heating to a desired length and profile, it is then cooled.

Figure 4:
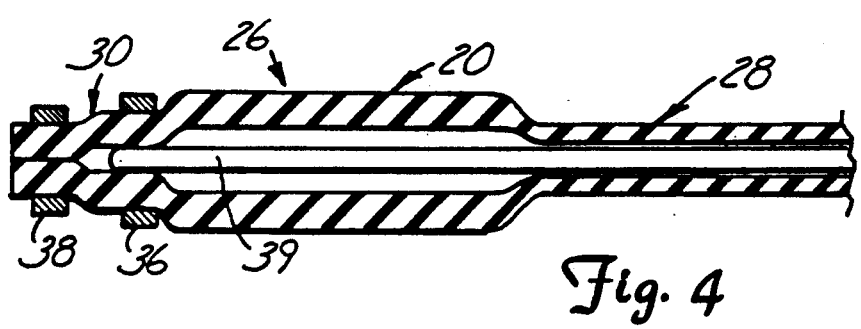
FIG. 4 illustrates a partial side view, in section, of a second end portion of the tubing element of FIG. 2, prior to stretching thereof.

The second end segment 30 is stretched in much the same fashion as the first end segment 28. An internal support mandrel 39 having a second diameter is positioned within the first end segment 28 and intermediate segment 20 of the tubing element 26 (as shown in FIG. 4). The support mandrel 39 has a smaller diameter than the support mandrel 32 so that it can be readily inserted into the already stretched (and now smaller in internal diameter) first end segment 28 of the tubular element 26. The body clamp 36 is mounted about a distal end of the support mandrel 39, compressing a portion of the intermediate segment 20 onto the support mandrel 39. The end clamp 38 is mounted about an outer end of the second end segment 30, which is then heated while urging the body clamp 36 and end clamp 38 apart (as shown by arrow 31 in FIG. 5). Again, the separation of the clamps longitudinally stretches the heated second end segment 30 to a smaller inner and outer diameter.

Figure 5:
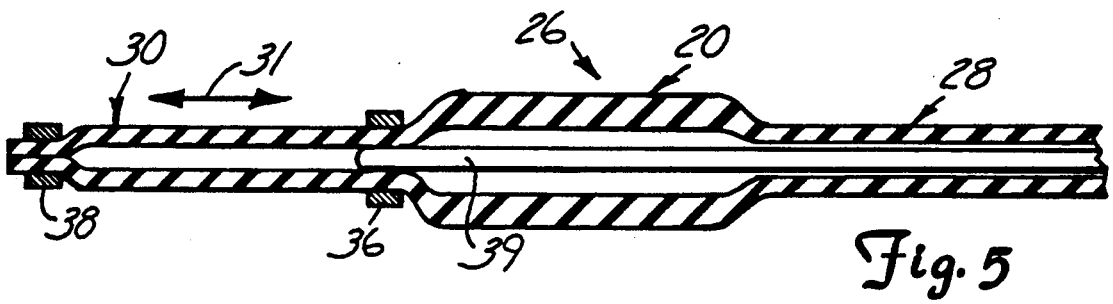
FIG. 5 illustrates the tubing element of FIG. 4 after the second end portion thereof has been stretched.

Because the support mandrel 39 is smaller than support mandrel 32, the second end segment 30 can be made smaller than the first end segment 28, as illustrated in FIG. 5. The size of the support mandrel 39 does not directly determine the inner diameter of the stretched second end segment 30 (because the mandrel 39 is not really contained within the segment 30), but it does provide a base inner diameter adjacent the clamp 36 to facilitate stretching. As before, the clamps constrict to maintain their grip on the second end segment 30 as the clamps are separated from one another, and the clamps are formed or treated to prevent damage to the tubing element 26 during processing. Further, variations in the amount of stretch can be made with alternative heating times, temperatures, by repeating the number of heating and urging cycles and/or by controlling the distance of clamp separation. Once second end segment 30 has been worked by stretching to its desired length and profile, it is then cooled.

Figure 6:
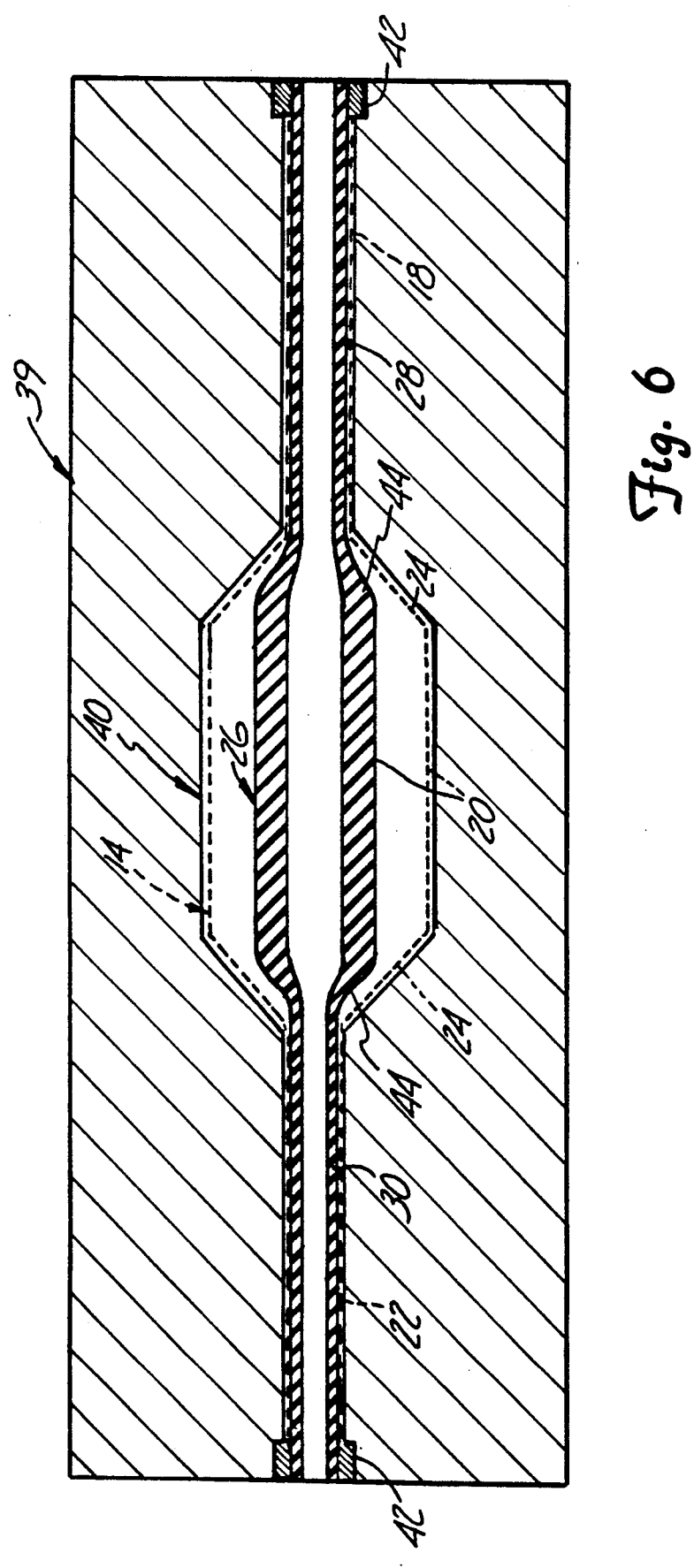
FIG. 6 illustrates, in section, the form of a cavity used to define the expandable balloon section of the tubing element, in accordance with the present invention.

After the end segments of the tubing segment 26 have been stretched, it is placed in a balloon mold 39, which has an enlarged diameter cavity 40 for reception of the unstretched intermediate segment 20, as shown in FIG. 6. The first end segment 28 and second end segment 30 are fixed at their respective ends by fixation clamps 42 such that the intermediate segment 20 is centered within the cavity and so that, upon further heating of the tubing segment 26, the stretched end segments will not shrink longitudinally. As seen in FIG. 6, transition areas 44 of varying diameters and wall thickness are formed in the tubing segment 26, between the intermediate segment 20 and the end segments 28 and 30. These transition areas 44, between the stretched and unstretched portions of the tubing segment 26, are also positioned within the enlarged cavity 40 and ultimately form the cone-shaped end portions 24 of the balloon 14.

The tubing segment 26 is then heated and pressurized in the mold 39 (i.e., blow-molded) causing it to expand radially outwardly against the walls of the cavity 40. The intermediate segment 20 and cone-shaped end portions 24 assume a shape (the shape of the cavity) which defines the distensible portion of the balloon 14 in an inflated state (as shown with dashed lines). The cone-shaped end-portions 24 are thus formed to a smaller wall thickness by the radial stretching of the transition areas 44 during blow molding. Likewise, the intermediate segment 20 attains a smaller wall thickness as it is stretched radially outwardly in the cavity 40. The process of heating and pressurizing also expands the first end segment 28 and the second end segment 30 of the tubing element 26 within the cavity 40 so that they define the desired shapes of waist segment 18 and distal segment 22 of balloon 14 (as also shown with dashed lines). The tubing segment 26 (which now has assumed the molded shape of the cavity 40) is then cooled to achieve its final desired dimensions, and the balloon 14 is ready for attachment to the shaft 12 and for further processing (i.e., deflating, wrapping, compression sleeve installation etc.).

As illustrated in FIGS. 2-6, the first end segment 28 of the tubing element 26 is typically larger in diameter than the second end segment 30, which is a result of stretching one segment farther than the other and using mandrels with different diameters. As can be appreciated, the more stretch or elongation of a segment, the smaller its diameter will be. FIG. 6 illustrates the waist segment 18 being formed from the first end segment 28 of the tubing element 26, the larger diameter segment of the two formed. While this is preferable, it is also possible to form the waist segment 18 from the second end segment 30 (and the distal portion 22 from the first end segment 28). The particular balloon formation depends upon the needs and demands of a particular catheter.

After the tubing material has been extruded from the extruder it is preferably irradiated before being cut into the tubing segments 26. Alternatively, each tubing segment 26 can be irradiated after being stretched but prior to formation of the balloon 14 as illustrated in FIG. 6. Irradiation (e.g., electron bombardment via an electron beam) is a process (e.g., electron beaming) of exposing the tubing material (or tubing element 26 if the material has been cut and stretched) to ionizing radiation. Irradiation enhances the mechanical characteristics of the balloon (such as balloon 14) to give strength by "locking in" the axial orientation of the molecules within the tubing material. Thus, in a preferred embodiment the tubing material is irradiated and then cut into segments, and the tubing segments are then stretched and further formed as described above.

By way of example, a preferred method for practicing the invention uses a polymeric tube formed with a draw-down ratio of 2:1 from a polyolefin copolymer material. To create a balloon which, when inflated, has a profile of approximately 3.0 mm at 6 atmospheres pressure, the extruded tubing has an inner diameter of 0.0241 inches and an outer diameter of 0.0395 inches. The tubing is irradiated and then cut into the desired length for forming a balloon and its proximal and distal waist segments.

To further form one of the segments, a mandrel is inserted into one end of the tubing as discussed above, and spaced clamps are secured about the tubing and mandrel and an adjacent end of the tubing. The segment of the tubing to be stretched is heated and the clamps are urged apart so that the segment being stretched is elongated by approximately 100% of its original length. Such elongation may be the result of a single heat and stretch procedure, or repeated heatings/stretchings of that segment. After the tubing segment has been so stretched, however, it is then cooled, and the resultant dimensions of the stretched segment are an inner diameter of 0.0170 inches and an outer diameter of 0.0279 inches. An additional segment of the tubing may be stretched, if desired. In this example, the distal waist segment and proximal waist segment, while they may differ in length, are each stretched approximately 100% from their respective original lengths, to achieve the same resultant post-stretched inner and outer diameter dimensions.

After the stretching steps are completed, the tubing is secured within a blow-mold and heated and pressurized internally to expand the tubing material outwardly into the defined cavity of the mold. In this example, the cavity mold for the stretched distal segment of the tubing has a smaller outer diameter than the cavity mold diameter for the stretched proximal segment of the tubing, while the mold diameter for the intermediate balloon segment is defined as approximately 3.0 mm. Accordingly, the molded and post-mold dimensions of the tubing (which sometimes exhibits negligible shrinkage after molding and cooling) are, for the distal segment, an inner diameter of 0.1750 inches and an outer diameter of 0.0285 inches, and for the proximal segment, an inner diameter of 0.0220 inches and an outer diameter of 0.315 inches.

After the balloon has been further treated, folded and compressed, it has an outer profile (diameter) of approximately 0.034 inches. As noted above, the distal segment of the balloon has an outer diameter of 0.0285 inches while the proximal segment has an outer diameter of 0.0315 inches. Thus, the distal segment has a smaller outer diameter than the balloon itself which aids in threading the balloon into a small stenosis opening. It should be noted that without stretching, the outer diameter of the distal portion of the tubing would be 0.0395 inches, which is larger than the compressed folded profile of the balloon (0.034 inches). In addition to reducing the overall profile of the proximal and distal segments of the balloon, the stretching thereof also results in making those portions of the catheter more flexible and thereby easier to work into a tight or tortuous stenosed arterial lumen.

The present inventive method provides significant advantages over prior art balloon manufacturing methods. The invention allows the distensible portion of a balloon to be correctly manufactured while providing small diameters and thinner walls at the proximal and distal ends thereof. There is continuing need to reduce balloon and shaft profiles so that tighter arterial lesions may be crossed and treated. This method allows for the formation of a thin-walled balloon having a flexible tapered end. In addition the distal and proximal end portions of the balloon have thinner walls and reduced profiles, and are thus more flexible. This allows the formation of a balloon with a smaller uninflated profile to be attained, while maintaining enhanced flexibility in the distal and proximal segments of the balloon. The thinner walls and reduced diameters also allow tighter protector or compression sleeves to be installed over the balloon to further reduce its uninflated profile. Both the lower profile of the balloon and the taper at the distal end allows easier passage into and across a stenosis. Consequently, the inventive method allows the manufacture of balloon catheters which can cross tighter lesions than was previously possible, the use of which will allow angioplasty to be used in patients that previously required a more intrusive surgical procedure.

Although the present invention has been described with reference to preferred embodiments, workers skilled in the art will recognize that changes may be made in form and detail without departing from the spirit and scope of the invention.

What is claimed is:

1. A method of forming a stretched tubing element used for forming a balloon portion of a balloon dilatation catheter from a tubing element having a first outer diameter wherein the tubing element has a first end segment, an intermediate segment, and a second end segment, the method including the steps of:

positioning a first internal support mandrel having a first diameter within the second end and intermediate segments of the tubing element;

attaching a body clamp about the first support mandrel and intermediate segment of the tubing adjacent a distal end of the first support mandrel;

attaching an end clamp to the first end segment adjacent an outer end thereof;

heating the first end segment;

urging the body clamp and end clamp longitudinally apart thereby stretching the first end segment longitudinally to lengthen said first end segment and reduce the outer diameter thereof to a second, smaller outer diameter;

cooling the first stretched end segment;

positioning a second internal support mandrel, having a second diameter which is smaller than the first support mandrel, within the stretched first end and intermediate segments of the tubing element;

attaching the body clamp about the second support mandrel and intermediate segment of the tubing element adjacent a distal end of the second support mandrel;

attaching the end clamp to the second end segment adjacent an outer end thereof;

heating the second end segment;

urging the body clamp and end clamp longitudinally apart thereby stretching the second end segment longitudinally to lengthen said second end segment and reduce the outer diameter thereof to a third outer diameter smaller than the second outer diameter; and cooling the second stretched end segment to form the stretched tubing element, wherein a major extent of the intermediate segment has not been stretched.

2. The method of claim 1, wherein the heating and urging steps are repeated for the first end segment.

3. The method of claim 1, wherein the heating and urging steps are repeated for the second end segment.

4. The method of claim 1, wherein the tubing element is pre-formed by drawing a tubing material from an extruder using a predetermined draw-down ratio and rate of extrusion.

5. The method of claim 4, wherein the draw-down ratio is 2:1.

6. The method of claim 1, wherein the tubing element is irradiated before stretching.

7. The method of claim 1, wherein the tubing element is irradiated after stretching.

8. The method of claim 1, and further comprising forming the balloon portion from the stretched tubing element comprising the steps of:

containing the stretched tubing element in a mold cavity so that the intermediate segment of the stretched tubing element is positioned within an enlarged portion of the mold cavity corresponding in shape to a desired inflated profile for the balloon;

heating the stretched tubing element;

pressurizing the stretched tubing element to expand the intermediate segment thereof radially outwardly into the enlarged portion of the mold cavity thereby forming the balloon portion; and cooling the balloon portion.

9. The method of claim 8, wherein the first end and second end segments are fixed relative to the cavity at their respective ends prior to the pressurizing and heating steps.

10. The method of claim 8 wherein the mold cavity includes enlarged diameter portions for the stretched first end segment and stretched second end segment so that upon pressurization of the stretched tubing element, the first and second stretched end segments are expanded radially outwardly into the enlarged diameter portions.

11. A method of forming a balloon for use on a balloon dilatation catheter form a tubing element having a first outer diameter wherein the tubing element has a first end segment, an intermediate segment, and a second end segment, the method including the steps of:

positioning a first internal support mandrel having a first diameter within the second end and intermediate segments of the tubing element;

attaching a body clamp about the first support mandrel and intermediate segment of the tubing element adjacent a distal end of the first support mandrel;

attaching an end clamp to the first end segment adjacent an outer end thereof;

heating the first end segment;

urging the body clamp and end clamp longitudinally apart to lengthen the first end segment and reduce the outer diameter thereof to a second, smaller outer diameter to form a stretched first end segment without stretching the intermediate segment;

cooling the stretched first end segment;

positioning a second internal support mandrel having a second diameter within the stretched first end segment and the intermediate segment of the tubing element;

attaching the body clamp about the second support mandrel and intermediate segment of the tubing element adjacent a distal end of the second support mandrel;

attaching the end clamp to the second end segment adjacent an outer end thereof;

heating the second end segment;

urging the body clamp and end clamp longitudinally apart to lengthen the second end segment and reduce the outer diameter thereof to a third outer diameter smaller than the second outer diameter without stretching the intermediate segment to form a stretched tubing element having stretched first and second end segments and a non-stretched intermediate segment;

cooling the second stretched end segment;

containing the stretched tubing element in a mold cavity so that the intermediate segment of the stretched tubing element is positioned within an enlarged portion of the mold cavity corresponding in shape to a desired inflated profile for the balloon;

heating the stretched tubing element;

pressurizing the stretched tubing element to expand the intermediate segment thereof radially outwardly into the enlarged portion of the mold cavity thereby forming the balloon; and cooling the balloon.

* * * * *